United States Patent
Pagedas

[19]

[11] Patent Number: 6,015,428
[45] Date of Patent: Jan. 18, 2000

[54] INTEGRALLY FORMED SUTURE AND SUTURE LOCK

[75] Inventor: Anthony C. Pagedas, 8401 W. Edgerton, Greendale, Wis. 53129

[73] Assignee: Anthony C. Pagedas

[21] Appl. No.: 09/089,916

[22] Filed: Jun. 3, 1998

Related U.S. Application Data

[60] Provisional application No. 60/048,489, Jun. 3, 1997.

[51] Int. Cl.[7] ................................................ A61B 17/04
[52] U.S. Cl. ............................................................ 606/232
[58] Field of Search .................................. 606/230, 231, 606/232, 233, 139

[56] References Cited

U.S. PATENT DOCUMENTS

| | | | |
|---|---|---|---|
| 5,413,585 | 5/1995 | Pagedas | 606/232 |
| 5,669,935 | 9/1997 | Rosenman et al. | 606/232 |
| 5,725,556 | 3/1998 | Moser et al. | 606/232 |
| 5,741,301 | 4/1998 | Pagedas | 606/232 |

*Primary Examiner*—Michael Buiz
*Assistant Examiner*—(Jackie) Tan-Uyen T. Ho
*Attorney, Agent, or Firm*—Ryan Kromholz & Manion, S.C.

[57] ABSTRACT

A molded plastic one-piece self adjusting self locking suture lock to be used with surgical suture thread and suture needle, said self adjusting self locking suture lock comprising: a body having a front side, a back side, a first edge, a thread retaining opening, and a stitch lock opening; the thread retaining opening having a thread opening slightly smaller in diameter than said suture thread and a slot extending outwardly from said thread opening to said first edge. The stitch lock opening being right cylindrical and having an outer edge on said front side. The body having a plurality of integral tongues connected to said outer edge of the stitch lock opening near said front side and extending diametrically inward at an angle from said front side toward said back side. The tongues being of sufficient dimension and number to occupy substantially the entire circumference of the outer edge. Each of said tongues having a conical sectional shape such that the plurality of tongues connected near the outer edge of the front side form a conical structure having an approach opening on this front side larger than an exit opening on the back side.

7 Claims, 12 Drawing Sheets

INTEGRALLY FORMED SUTURE AND SUTURE LOCK

Benefit of prior provisional application Ser. No. 60/048,489 filed on Jun. 3, 1997, now abandoned, is claimed pursuant to 37 CFR § 1.78 (a)(3).

BACKGROUND OF THE INVENTION

The need for this invention arises from surgical practice, particularly surgical practice using laparoscopic instruments involving small incisions, with a television camera inserted in one of the incisions to view the field of the operation inside the patient and surgical instruments inserted in other incisions and manipulated from outside the patient's body using a TV screen visualization, usually enlarged, to guide the work.

Anything that can reduce the number of steps to be performed in such an operation can markedly reduce the stress, both on the patient and on the doctor. Surgeons performing such operations are under considerable stress because remote manipulation using TV for visualization, rather than seeing the site of the operation directly requires the learning of a great many techniques that are radically different from those performed when the surgical site is open to view. These include indirect hand-eye coordination, and cooperation between surgeons to place and secure sutures.

The placing of sutures during a laparoscopic procedure typically requires two surgeons to cooperate in a multi-step process performed with multiple surgical instruments to manipulate the needle and the suture and pass it back and forth from one to the other, cooperation in tying the knot, etc. This invention arose from the difficulty of such manipulations.

Additionally, coagulation and clips, such as "hemo clips", have reduced many of the needs for endoscopic suturing. However, when one considers the need to suture repair ovaries, uterus, seromuscular defects, enterotomies, systomies, pelvic defects, various suspension procedures i.e. vaginal vault and sacrospinous, one must realize there is a continual need to keep the art of endoscopic suturing to the forefront. The endoscopic suturing must be so simple that it be easily learned, hence easily remembered. The learning curve in endoscopic suturing is inversely proportional to the number of steps required to do the suturing; i.e. the fewer steps required the easier it is to learn and teach the endoscopic suturing technique. It is the purpose of the present invention to provide a structure, which makes it easier to learn and teach an endoscopic suturing technique.

U.S. Pat. No. 5,413,585 is believed, presently, to be the closest prior art reference.

SUMMARY OF THE INVENTION

The present invention is a suture lock and a suture lock holder to be used with surgical thread and needles and which relies primarily on a one piece specialized lock having a body with a front side, a back side, a first edge, a thread retaining opening and a stitch lock opening. The thread retaining opening is slightly smaller than the suture thread to be used with the suture lock and has a slot extending from the opening itself to the first edge of the body of the suture lock device.

In contrast to the embodiments taught in U.S. Pat. No. 5,413,585, a plurality of tongues are deployed within a right cylindrical stitch lock opening. The plurality of tongues are integrally connected to an outer edge of the stitch lock opening near the front side of the body of the suture lock device. The tongues extend diametrically inward into the stitch lock opening at an angle from the front side of the body towards the back side of the body and have a conical sectional shape such that the tongues form a partial conical structure within the stitch lock opening. The conical structure deployed within the stitch lock opening has an approach opening on the front side of the body that is of a larger diameter than an exit opening of the conical structure that is located toward the back side of the body of the suture lock. In addition, the conical structure defined by the tongues extends around substantially the entire circumference of the outer edge of the stitch lock opening.

The flexible tongues project into the stitch lock opening and are inclined in the direction that the suture needle follows when it is inserted first into the larger approach opening to later pass through the smaller exit opening. Each flexible tongue freely allows the suture material to pass through the stitch lock opening by deflecting the tongue as the suture material passes by it. However, the springiness of each tongue and the engagement of each tongue edge with the suture material prevents the withdrawal of the suture material. The finished suture is under tension and so deflects the tongues upward into the stitch lock opening, jamming the suture material against the other tongues. The equivalent of a knot is thereby achieved.

The principal advantage of my improvement is that by providing a plurality of tongues as disposed within the stitch lock opening, various diameters of suture materials and suture needles can be accommodated by the same suture lock. Also, the thread or suture material is held generally at the center of the stitch lock opening. Whereas the self-locking suture lock as disclosed in U.S. Pat. No. 5,413,585 was limited to the use of a particular diameter of suture needle and suture material or to a very limited range of diameters of suture needles or materials, the present improvement can accommodate a wider range of suture needles and suture materials.

Alternatively, the present invention may be described as a molded plastic one-piece self adjusting self locking suture lock to be used with surgical suture thread and suture needle, said self adjusting self locking suture lock comprising a body having a front side, a back side, a first edge, a thread retaining opening, and a stitch lock opening. The thread retaining opening having a thread opening slightly smaller in diameter than said suture thread and a slot extending outwardly from said thread opening to said first edge. The stitch lock opening being right cylindrical and having an outer edge on said front side. The body having a plurality of integral tongues connected to said outer edge of the stitch lock opening near said front side and extending diametrically inward at an angle from said front side toward said back side. The tongues being of sufficient dimension and number to occupy substantially the entire circumference of the outer edge. Each of said tongues having a conical sectional shape such that the plurality of tongues connected near the outer edge of the front side form a conical structure having an approach opening on this front side larger than an exit opening on the back side.

Additionally, the self locking suture lock may have a front side of said body which is distinctively colored around said stitch lock opening. Further, the self locking suture lock may have a body having arms adjacent said thread retaining opening for clamping suture thread in said thread retaining opening.

Alternatively, the present invention may also be described as a one-piece self adjusting self locking suture lock to be used with surgical suture thread and a suture needle, said self adjusting self locking suture lock comprising a body having a front side, a back side, and a first edge. The body having a first opening said first opening having a thread opening slightly smaller in diameter than said suture thread, and a slot extending outwardly from said thread opening to said first edge. The body having a front side, a backside, a first edge, a thread-retaining opening, and a stitch lock opening. The thread retaining opening having a thread opening slightly smaller in diameter than said suture thread and a slot extending outwardly form said thread opening to said first edge. A body having a front side, a backside, a first edge, a thread retaining opening, and a stitch lock opening. The thread retaining opening having a thread opening slightly smaller in diameter than said suture thread and a slot extending outwardly form said thread opening to said first edge. The stitch lock opening being right cylindrical and having an outer edge on said front side. The body having a plurality of integral tongues connected to said outer edge of the stitch lock opening near said front side and extending diametrically at an angle from said front side toward said back side. The tongues being of sufficient dimension and number to occupy substantially the entire circumference of the outer edge. Each of said tongues having a conical sectional shape much that the plurality of tongues connected near the outer edge of the front side form a conical structure having an approach opening on this front side larger than an exit opening on the back side.

Alternatively, the present invention may be described as a molded plastic one-piece self adjusting self locking suture lock to be used with surgical suture thread and suture needle, said self adjusting self locking suture lock comprising a body having a front side, a back side, a first edge, a thread retaining opening, and a stitch lock opening. The thread retaining opening having a thread opening slightly smaller in diameter than said suture thread and a slot extending outwardly from said thread opening to said first edge. The stitch lock opening being right cylindrical and having mounted therein polymer plug, the polymer plug being an elastic substance capable of creating sufficient friction pressure on said suture material to secure a stitch.

Further, the self-adjusting self-locking suture lock holder may include a polymer plug, which is distinctly colored.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 1:
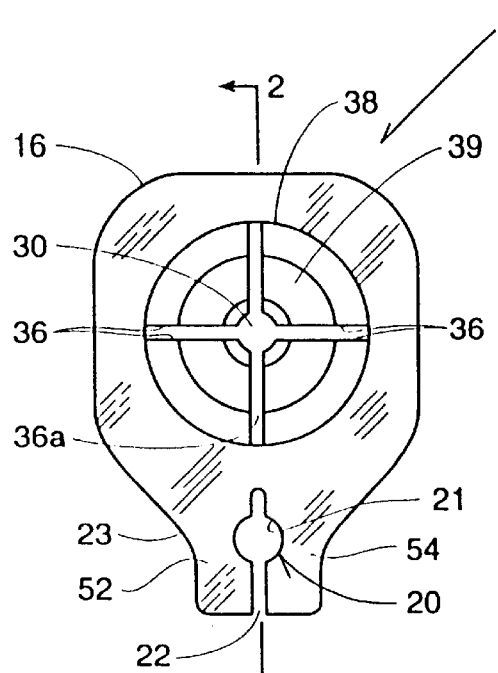
FIG. 1 is a plan view of the back of the self-adjusting, self-locking suture lock.

Referring to FIG. 1, the self locking suture lock 10 includes a body 16 having a first suture lock opening 20, a second stitch lock opening 30, a front side 32, and a back side 34. The second opening 30 is right cylindrical and has disposed within it a plurality of tongues 36.

Figure 2:
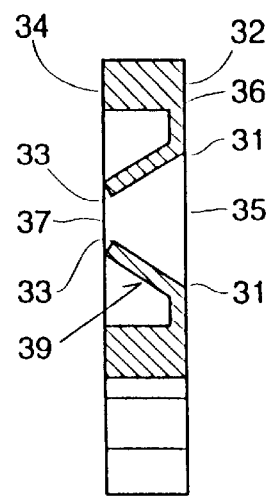
FIG. 2 is a side elevational view of the invention taken along line 2—2 of FIG. 1.
Figure 3:
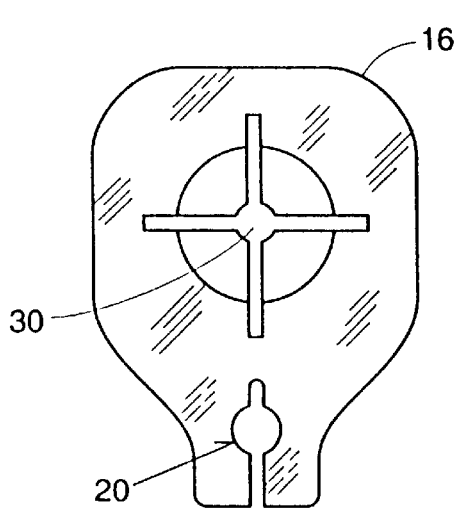
FIG. 3 is a plan view of the front of the invention.
Figure 4:
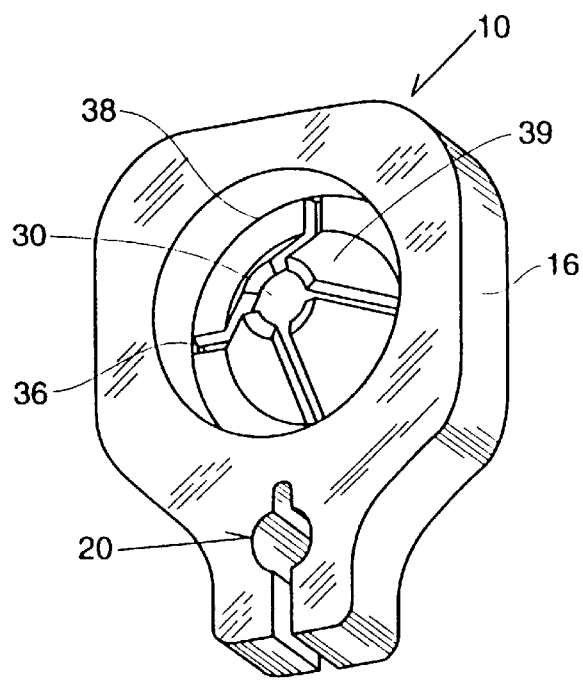
FIG. 4 is a three dimensional view of the invention clearly showing the cone-shaped structured formed by the tongues.

Referring also to FIG. 2, the area on the front side 32 of the body 16 around the second opening 30 between edges 31 and 33 may be colored differently than the rest of the body 16 in order to distinctly mark the difference between the front side 32 and the back side 34. This is so that the surgeon may distinguish the front side 32 from the backside 34 of the suture lock body 16. This helps to prevent the surgeon from inserting the suture thread 12 into the second opening 30 in the wrong direction, as does the tongue orientation.

As shown in FIG. 1, the first opening 20 has a circular thread opening 21 and a slot 22. The slot 22 projects inwardly from edge 23 to meet thread opening 21 and continue a short distance beyond the thread opening 21. The slot 22 creates two arms 52 and 54. The diameter of thread opening 21 is slightly smaller than the diameter of suture thread 12 (FIG. 2).

Suture thread 12 is threaded through thread opening 21. Following that, an attaching tool is used to clamp arms 52 and 54 together. The material that the self-locking suture 10 is formed from is deformable so that when the arms 52 and 54 are compressed together with an attaching tool or some other device, the diameter of thread opening 21 shrinks, clamping the body 16 to suture thread 12 and locking it in place on suture thread 12. The clamping of the suture thread 12 in the thread opening 21 completes the first step of a suture.

The tongues 36 in the second opening 30 are resilient pieces of body material that are connected integrally to the body 16 at the outer edge 38 of the second opening 30 nearer to the front side 32 than to the back side 34. The tongues 36, in the embodiment shown being four in number though this number may be varied, depend from the front side 32 of the body 16 and angle into this body 16 towards the back side 34 forming a partial conical structure 39 within the opening 30. The conical structure 39 formed by the tongues 36 being such that opening 30 has an approach open ing 35 larger than its exit opening 37. The exit opening 37 being slightly smaller than the smallest diameter suture thread 12 to be used with the self locking suture lock (FIG. 5).

Still referring to Figure it should be noted that a gap 36A is illustrated. It should be noted that gap 36A is optional and the tongues 36 could abut one another or even over lap each other when not engaging the needle 14 or the thread 12. Engagement of the needle 14 or the thread 12 may cause formation of the gap 36A as the tongues 36 are actively engaged or deflected.

Figure 5:
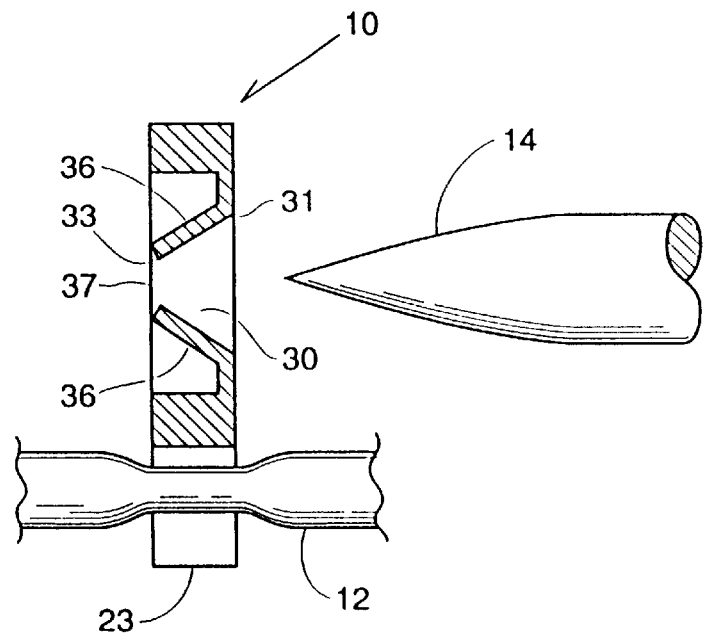
FIG. 5 shows the proper orientation during use of the invention.
Figure 6:
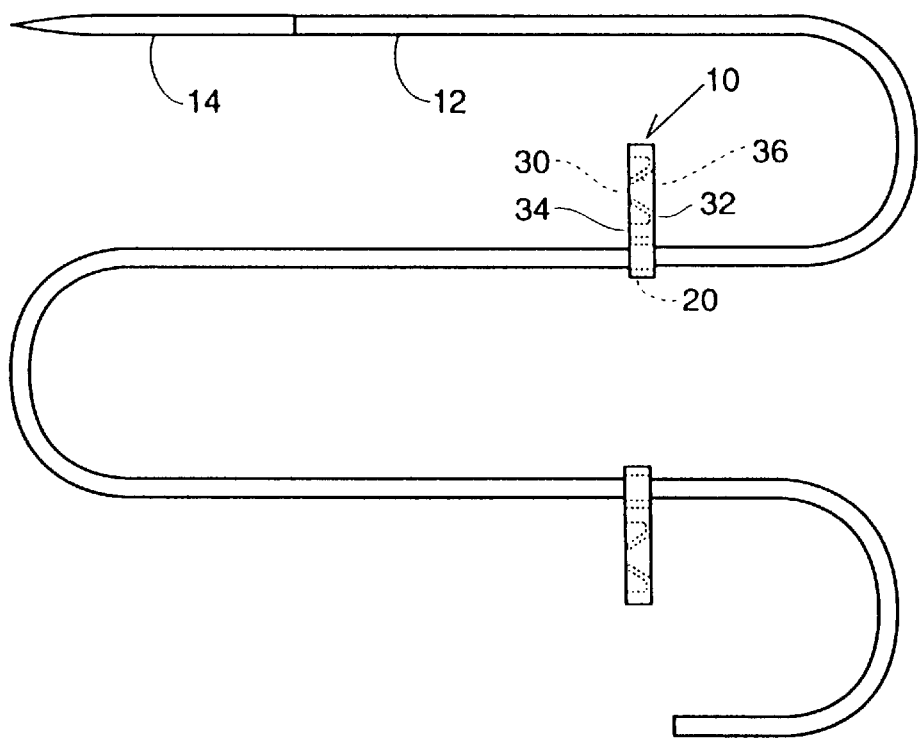
FIG. 6 shows the invention in use with suture needle of suture thread.
Figure 7:
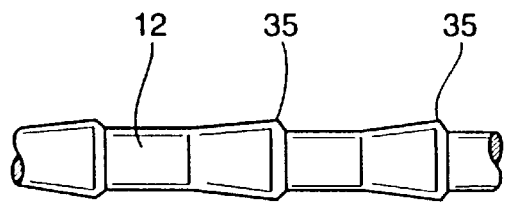
FIG. 7 is a side view of a suture thread showing a ridged structure, not to scale.
Figure 12:
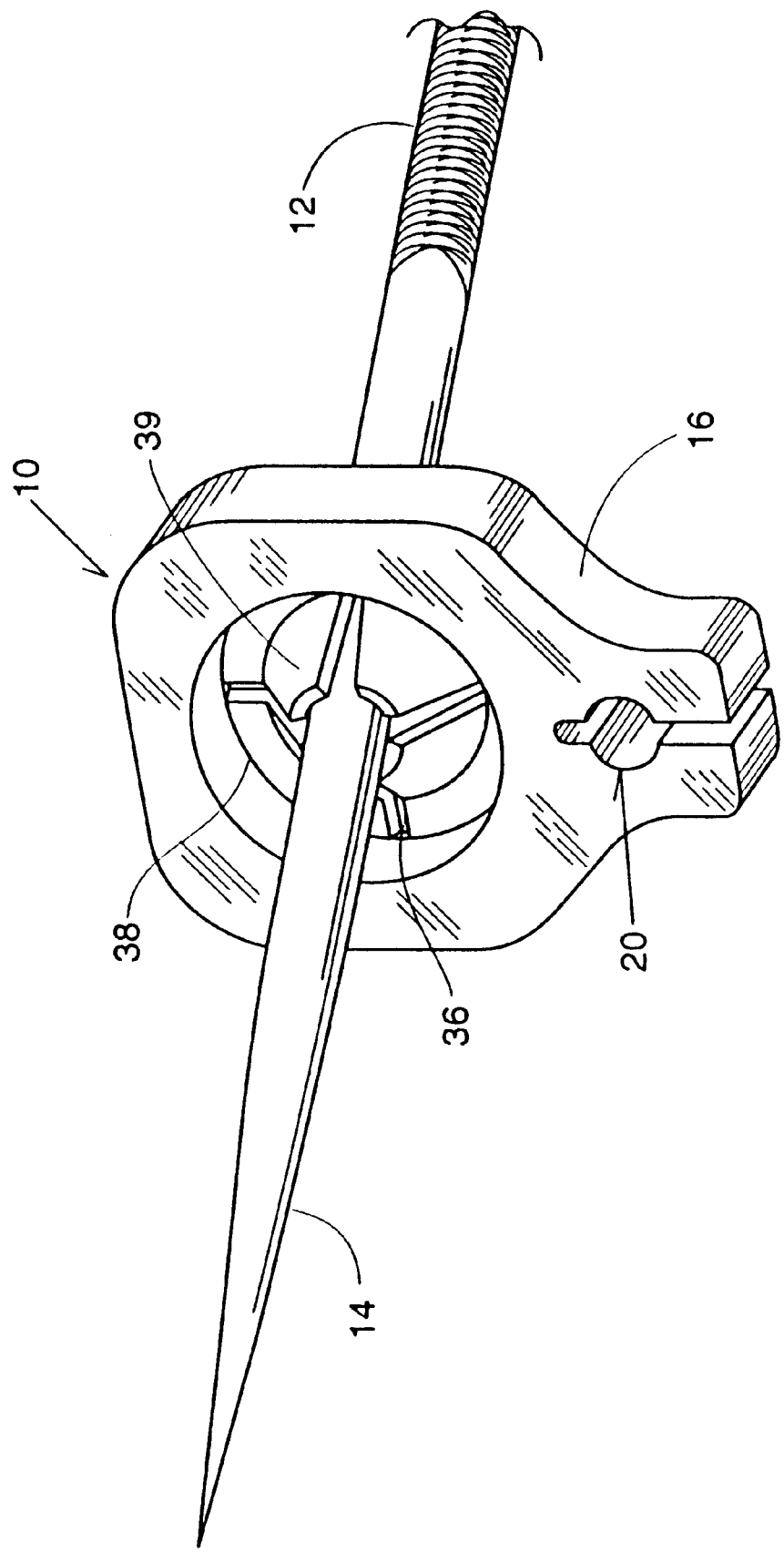
FIG. 12 shows a three dimensional view of a suture needle passing through the invention.
Figure 13:
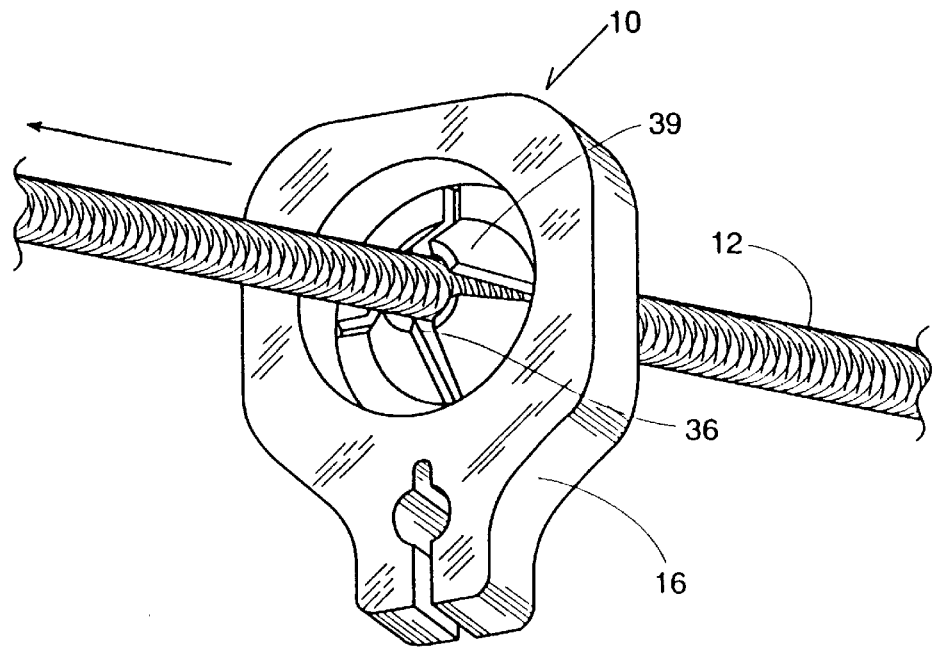
FIG. 13 shows the suture thread being drawn through the structure of the invention.
Figure 14:
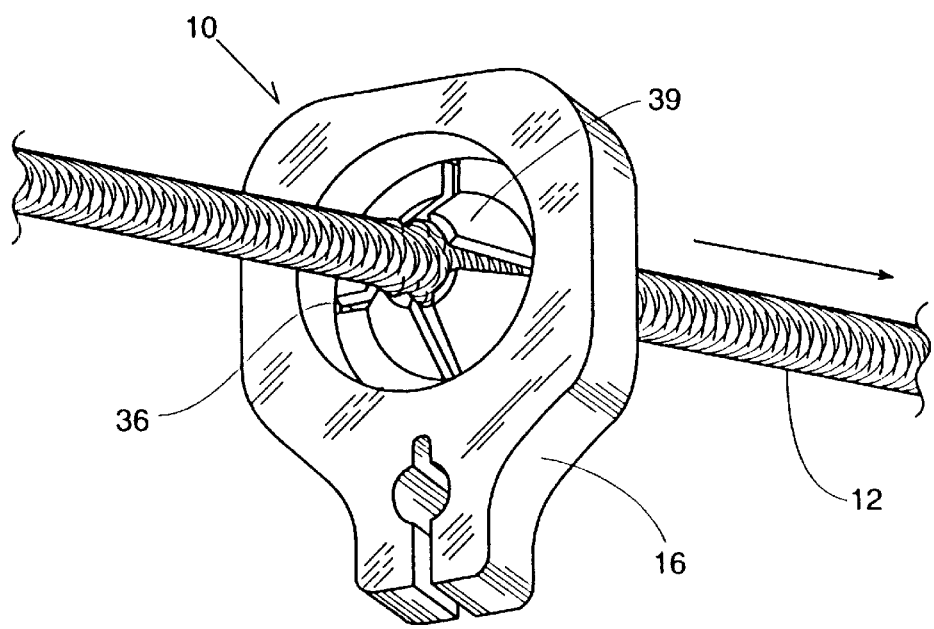
FIG. 14 shows the suture thread being drawn backwards to lock the suture thread in place thereby achieving the functional equivalent of a knot.

Referring to FIGS. 5 and 12 the conical structure 39 of the second opening 30 creates an approach that allows for easy passage of the suture needle 14 and suture thread 12 through the second opening 30 from the front side 32 to the back side 34. This deflects tongues 36 further toward the backside 34. The deflection of tongues 36 thus allows passage of the suture needle 14 and suture thread 12 through the second opening 30 (FIG. 13) from the front side 32 to the back side 34, but prevents passage of the suture thread 12 back through the second opening 30 from back side 34 to front side 32. The suture thread 12 is locked into the self locking suture lock (FIG. 14). Suture thread 12 may have tiny ridges 35 that are more inclined form the direction along thread 12 on the slope toward the tail of the thread than toward the needle (FIG. 7). Finally, the tongues 36 allow for more even dispersal of the force or tension, which results from engagement of the tongues 36 with the suture 12.

Figure 15:
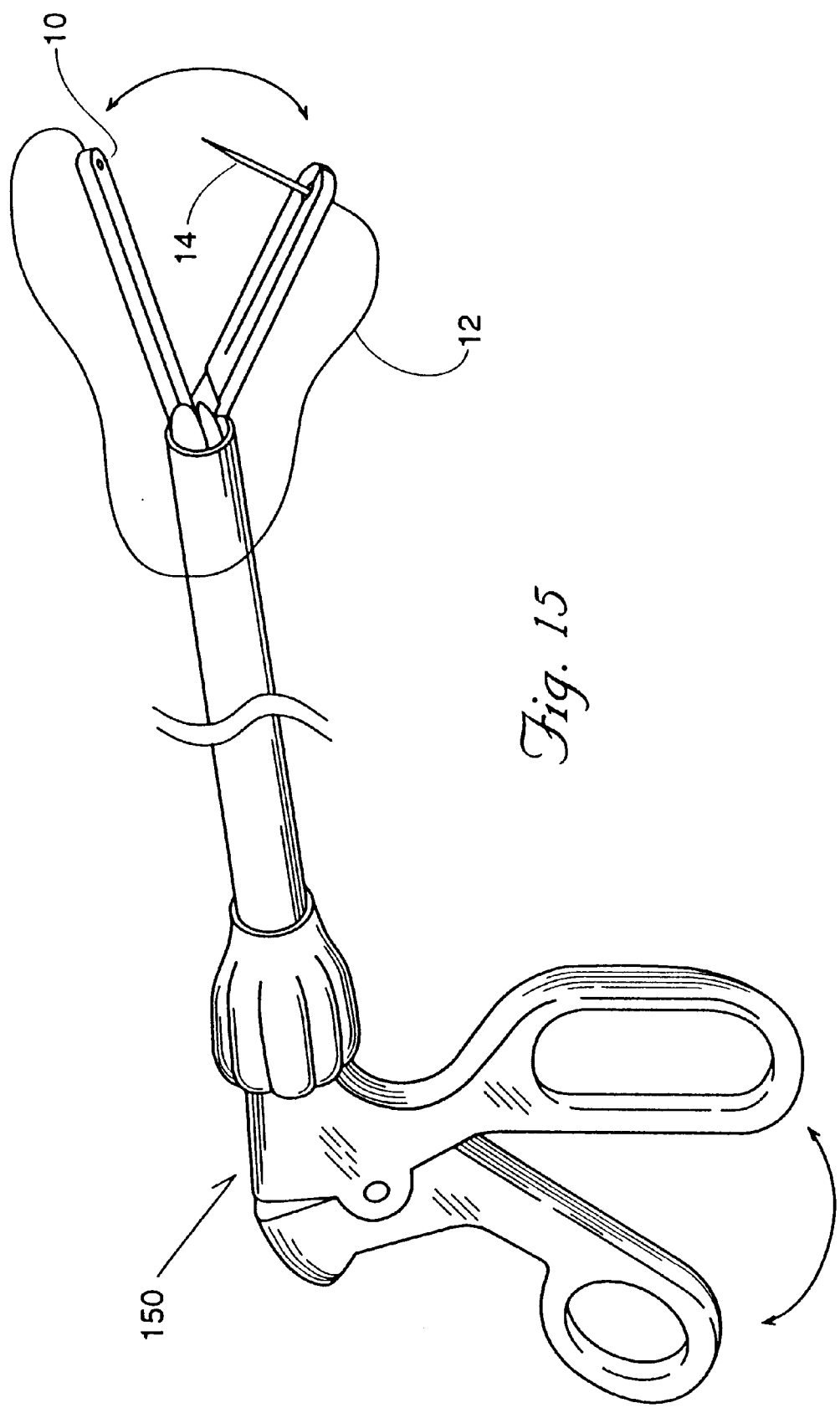
FIG. 15 shows the invention deployed for use with a laparascopic surgical instrument.

The self locking suture lock 10 works as follows. First, a self locking suture lock 10 is attached as previously described to a strand of suture thread 12 at a position determined by the surgeon, often at the end remote from the needle. A conventional straight or curved suture needle 14 is connected permanently to the free end of the suture thread 12. The combined suture and lock are introduced to the operative site, through a laparascopic tube if the operation is laparascopic. Second, the suture needle 14 and suture thread 12 are brought through the tissue to be sutured in the conventional manner. Third, the suture needle 14 and suture thread 12 are threaded through the second stitch lock opening 30 (FIG. 12) of the self locking suture 10 from the front side 32 to the back side 34 (FIG. 13) and pulled as tight as needed (FIG. 14). The suture is then complete, without the need for a second surgeon. An example of a typical laparascopic surgical instrument that the invention may be used with is shown in FIG. 15.

Additionally, since the suture thread 12 remains free at the end where the suture needle 14 is attached, another self locking suture lock 10 may be introduced to the operative site, if necessary through a laparascopic tube, and clamped at a desired position on the same suture thread 12. Following that, another stitch may be made and locked in the same manner as described above. Only the length of the thread 12 and the length of thread in each stitch limit the number of stitches.

Figure 8:
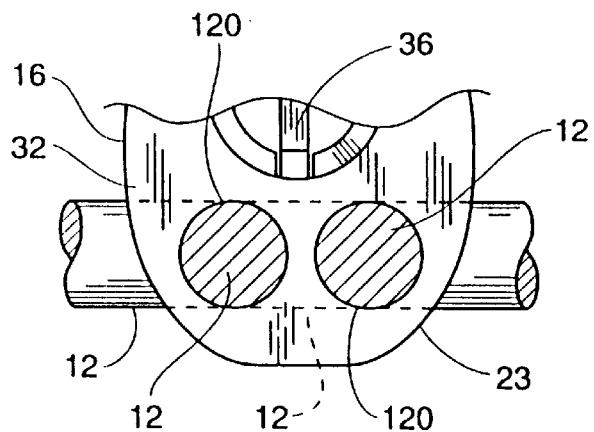
FIG. 8 is a fragmentary view like FIG. 1 showing an alternate embodiment.

FIG. 8 shows an alternative first opening that takes the form of a pair of holes 120 with sharp edges where holes 120 meet front side 32 and back side 34 of body 16 so that when thread 12 passes through both holes 120, tension on the suture holds thread 12 against movement.

Figure 9:
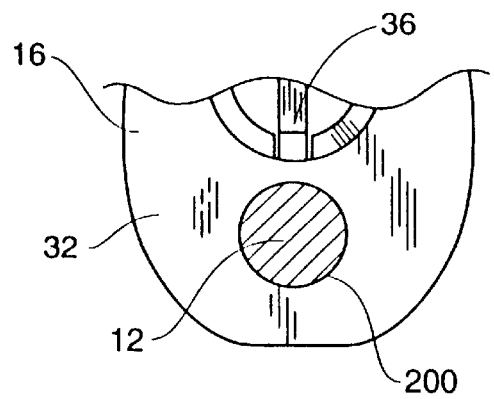
FIG. 9 is a fragmentary view like FIG. 1 showing an alternate embodiment.

FIG. 9 shows a further embodiment in which thread 12 is locked in first opening 20 by a solvent weld or heat weld 200 in a known manner. Sutures are commonly made of material capable of such treatment. The thread 12 can be welded or knotted.

Figure 10:
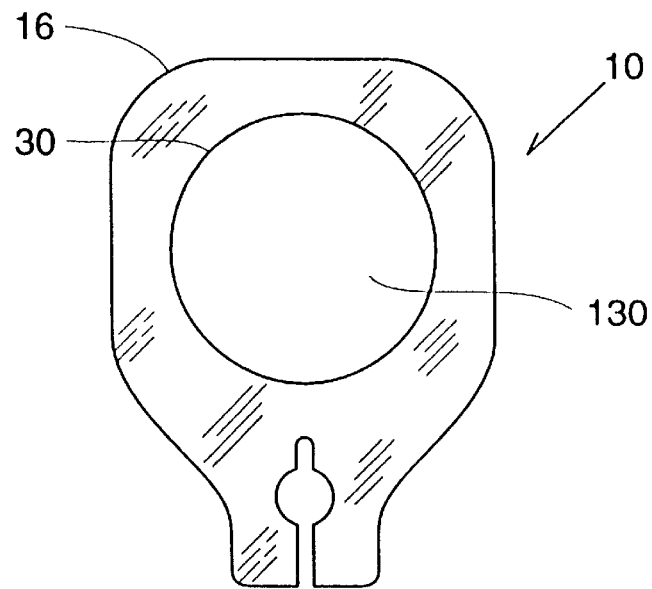
FIG. 10 shows a plan view of an alternate embodiment of the invention.
Figure 11:
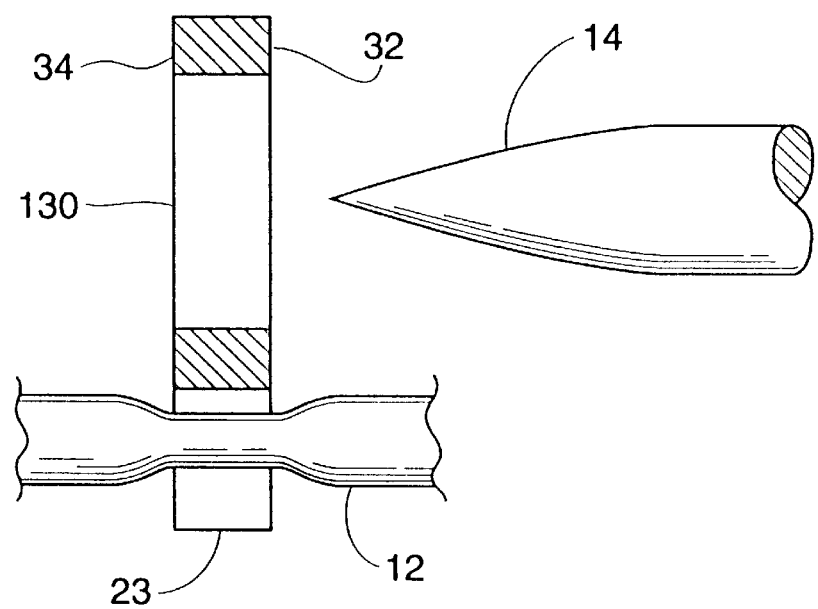
FIG. 11 shows a side elevational view of the alternate embodiment of the invention shown in FIG. 10.

FIG. 10 shows yet another embodiment in which right cylindrical opening 30 is completely filled with a polymer plug 130. The polymer plug 130 is capable of permitting the passage of a suture needle 14 and suture material 12 there through. Once the suture material 12 is pulled to its desired tension, the polymer plug 130, being elastic, squeezes the suture material thereby holding the suture material 12 in place by friction. Materials suitable for use as a polymer plug 130 are well known in the medical industry, one example being the self-sealing material used in the O-rings of certain IV injection ports. Another example of a suitable material is Prolene ™ polypropylene mesh manufactured by Ethicon, Inc. of Somerville, N.J. Prolene TM type meshes can be stretched across the stitch lock opening 30 in such a manner that suture thread can be passed through the stitch lock opening and the mesh, the mesh thereafter squeezing the suture thread to effectively hold the suture thread in place by friction. Other types of materials believed to be suitable, given by way of example and not by way of limitation are polypropylene, polyglycolate, and violet polydioxanone polymer. The major consideration given to the type of material chosen is the tolerance of the human body to fairly long exposure to the presence of this material. Materials that the human body can tolerate, or an animal body can tolerate should this device be used on non-humans, should be chosen.

One advantage of the embodiment depicted in FIGS. 10, 11, and 18–20 is that the suture lock opening 30 is bi-directional, the polymer plug 130 being capable of creating a friction hold on the suture material 12 to counter-act tension directed toward the front side 32 or the back side 34. See FIGS. 18–20. The polymer plug 130 may also be colored differently than the body 16, thereby making it easier to determine the location of the suture lock opening 30.

Figure 16:
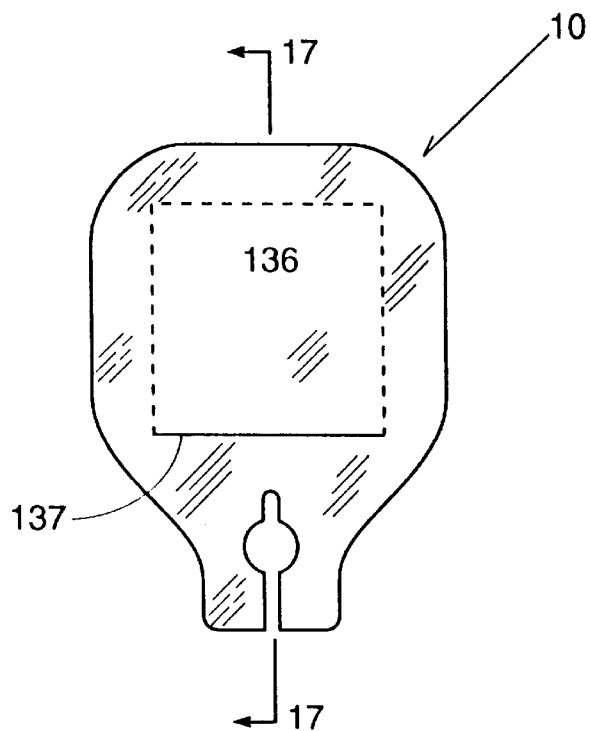
FIG. 16 is a plan view of the back of alternative embodiment of the self-adjusting, self-locking suture lock.
Figure 17:
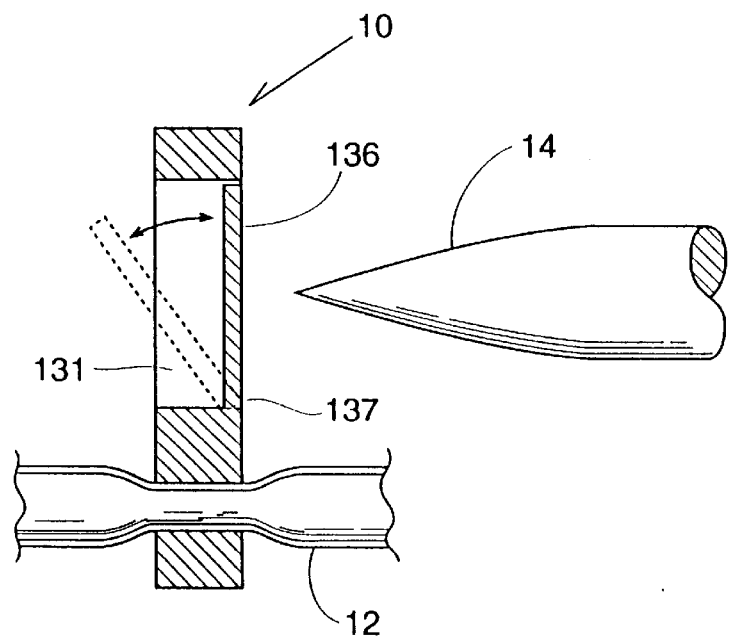
FIG. 17 is a side elevational view of the invention taken along line 17—17 of FIG. 16.
Figure 18:
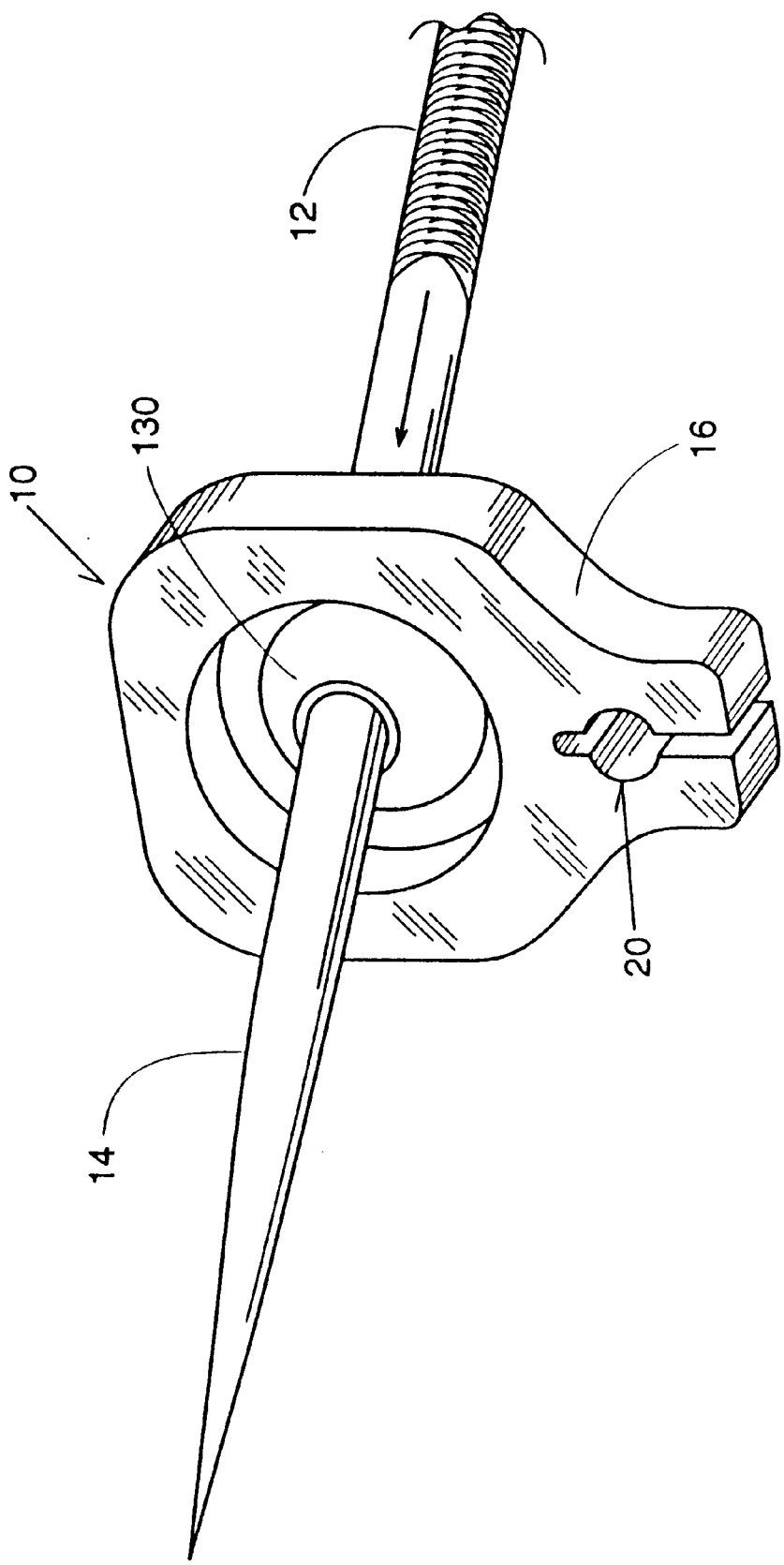
FIG. 18 shows the needle being drawn through the structure of the alternative embodiment of the invention shown in FIGS. 10 and 11.
Figure 19:
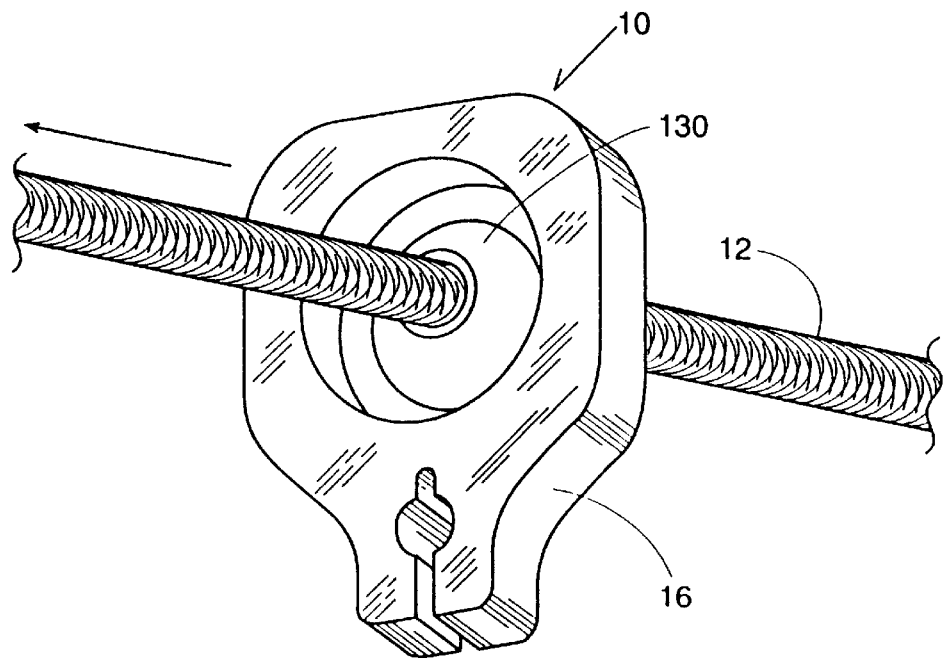
FIG. 19 shows the thread being drawn through the structure of the alternative embodiment of the invention shown in FIGS. 10 and 11.
Figure 20:
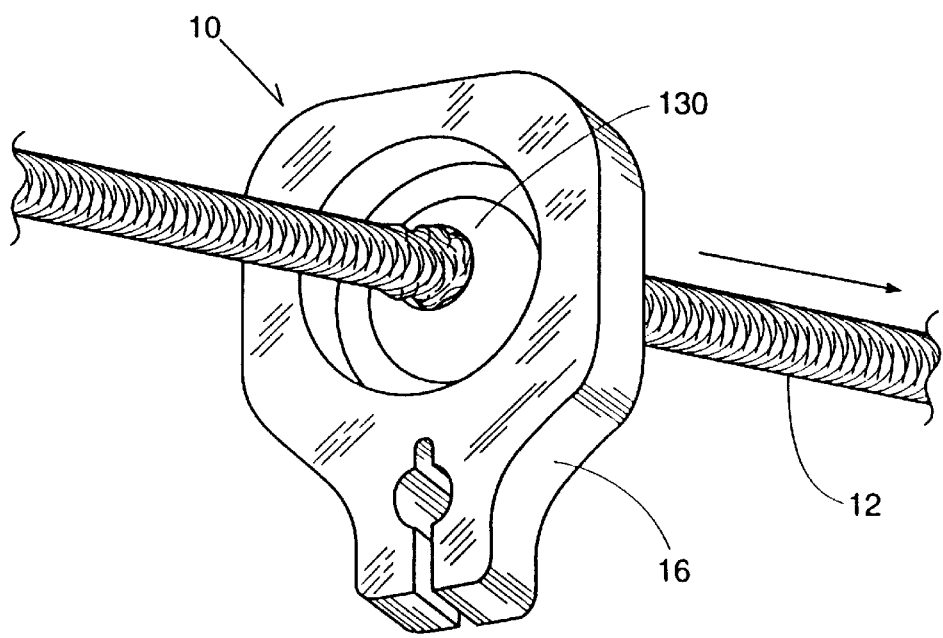
FIG. 20 shows the suture thread being drawn backwards and the resilient elastic material griping the suture thread, thereby achieving the functional equivalent of a knot.

FIGS. 16 and 17 illustrate another alternative embodiment wherein a single tongue 136, either flexible integral to or flexibly coupled to the suture lock 10 at flexing point 137. In this embodiment the needle 14 is pushed against tongue 136 and through opening 131 so that tongue 136 is depressed as illustrated in phantom in FIG. 17. This depressing of the tongue 136 results in engagement of the tongue 136 with the suture thread 12 thereby creating a frictional engagement with the suture thread 12 and hold the suture in place.

Figure 21:
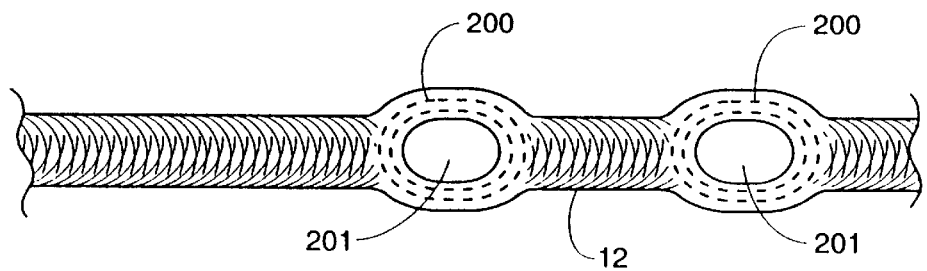
FIG. 21 illustrates another alternative embodiment wherein the suture thread has integral to its structure a spaced apart plurality of metallic or plastic rings which may be crimped after the needle and suture thread are looped therethrough, thereby achieving the functional equivalent of a knot.

Referring now to FIG. 21 another alternative structure is disclosed. In this embodiment crimpable rings 200 (shown in phantom), which may be made of titanium, polyglycolate, a VICRYL brand type material, Polyglactin 910, or other suitable material evident to a person skilled in the art reading this disclosure, are imbedded within the suture material 12 so that a series or plurality of openings 201 are presented in the thread 12. Accordingly, the needle 14 may, after passing through the desired tissue to be sutured, be drawn through the opening 201 a distance suitable to the surgeon making the stitch and then the crimpable ling 200 crimped with a crimping tool known in the surgical art, thereby locking the suture thread 12 in place without the necessity of tying a knot.

Figure 22:
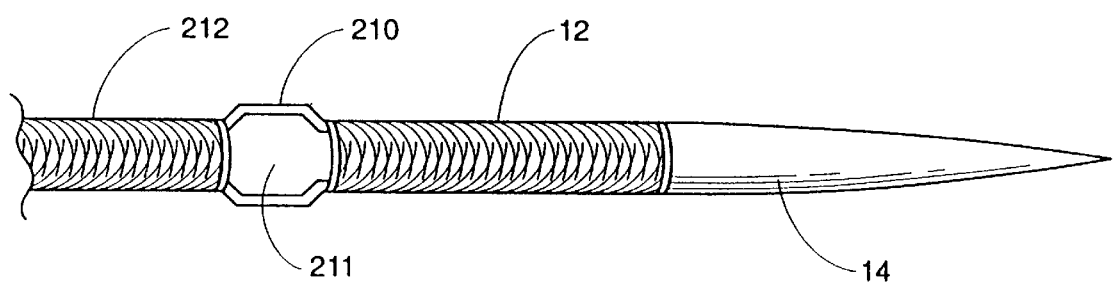
FIG. 22 illustrates another alternative embodiment wherein the suture thread includes a generally annular clip, like a hemo clip, crimped to the suture thread.

Referring now to FIG. 22 a design similar to that of FIG. 21 is illustrated except that a titanium or polyglycolate clip 210, not imbedded in the suture material 12, is used. The clip 210 is attached to the suture thread 12 in the same known way that needles 14 are either permanently or impermanently (as like a "pop off" needle) attached to the suture thread 12. Again, the needle 14 may, after passing through the desired tissue to be sutured, be drawn through the opening 211 a distance suitable to the surgeon making the stitch and then the clip 210 is crimped with a crimping tool known in the surgical art, thereby locking the suture thread 12 in place without the necessity of tying a knot. Another advantage of this embodiment is that the clip 210 acts to allow only a predetermined amount of thread 12 to be passed through the tissue since, as the thread 12 is drawn through the tissue the clip 210 will eventually engage the tissue as would a tailor's knot engage material being sewed. A tail 212 of suture material 12 may optionally be provided to present material which the surgeon may grasp with a laproscopic instrument to steady the clip 210 while it is crimped or to aid in steadying the clip 210 to make it easier to pass the needle 14 through the opening 211 as illustrated in FIG. 23; wherein two flaps of tissue 213 and 214 are being sutured.

Figure 23:
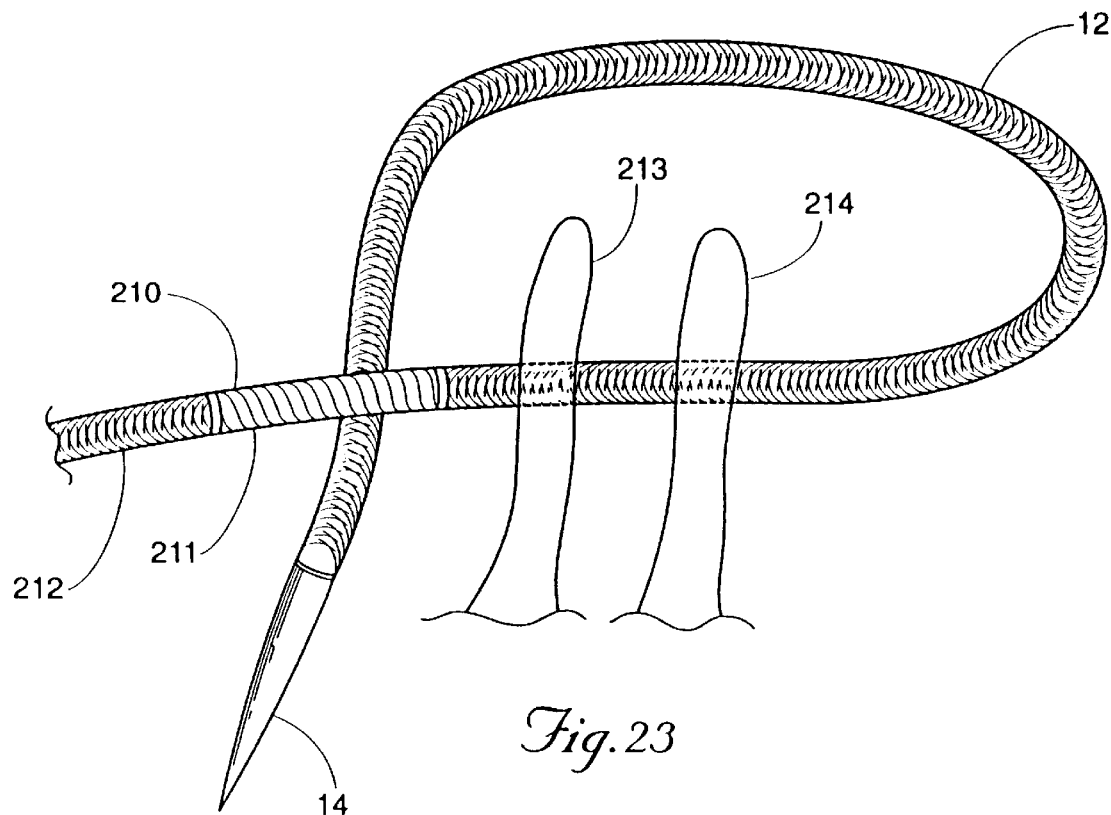
FIG. 23 illustrates the alternative embodiment of FIG. 24 being used to suture two flaps of tissue.
Figure 24:
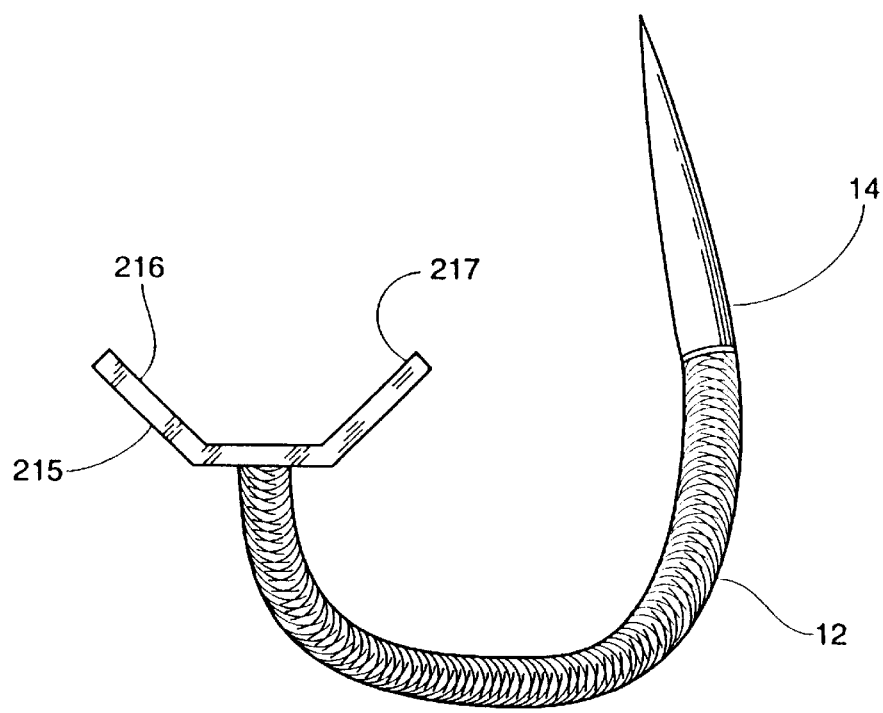
FIG. 24 illustrates another alternative embodiment wherein the suture thread, similar to the embodiment of FIG. 24, includes a clip like a hemo clip but the clip is generally C shaped, the thread being crimped to the C shaped clip.

Referring now to FIG. 24 an alternative structure similar to that disclosed in FIGS. 22 and 23 may be seen except that the clip 215 is generally C shaped. In this embodiment the suture thread 12 is passed between the horns 216 and 217 of the clip 215 and then the clip is crimped, thereby eliminating the need for a knot.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A self adjusting self locking suture lock to be used with surgical suture thread and suture needle, said self adjusting self locking suture lock comprising a body having a front side, a back side, a first edge, a thread retaining opening, and a stitch lock opening; the thread retaining opening having a thread opening slightly smaller in diameter than said suture thread and a slot extending outwardly from said thread opening to said first edge; the stitch lock opening having mounted therein an elastic plug capable of creating sufficient frictional pressure on said suture material to secure a stitch.

2. The self-adjusting self-locking suture lock holder of claim 1 including at least one elastic plug having a predetermined color.

3. A suture thread having at least one crimpable clip structure contained therein and wherein the crimpable clip structure defines an opening arranged to receive a transversely disposed thread and crimpable upon said thread.

4. The clip structure of claim 3 wherein said crimpable clip structure comprises an enclosed ring configuration.

5. The clip structure of claim 4 wherein the ring configuration is of open configuration including oppositely disposed laterally extending integral horns, said horns being capable of surrounding a portion of said thread and crimpable into secured relationship therewith.

6. The clip structure of claim 4, wherein said ring is embedded within the confines of said thread.

7. The clip structure of claim 4, wherein said ring is independent of said thread and having oppositely disposed portions secured to and linking separate portions of said thread.

* * * * *